United States Patent [19]

Dindi et al.

[11] Patent Number: 5,530,152
[45] Date of Patent: Jun. 25, 1996

[54] METHOD FOR MANUFACTURING ORGANOSILANES

[75] Inventors: Hasan Dindi; Stuart N. Milligan, both of Ponca City, Okla.

[73] Assignee: E. I. Du Pont de Nemours and Company, Wilmington, Del.

[21] Appl. No.: 390,339

[22] Filed: Feb. 17, 1995

[51] Int. Cl.[6] .................................................. C07F 7/08
[52] U.S. Cl. ............................................................ 556/479
[58] Field of Search ............................................. 556/479

[56] References Cited

U.S. PATENT DOCUMENTS

| | | | |
|---|---|---|---|
| 2,524,529 | 10/1950 | Krieble | 260/448.2 |
| 2,570,463 | 10/1951 | Ernsberger et al. | 260/448.2 |
| 3,925,434 | 12/1975 | Chuang | 556/479 |
| 4,161,572 | 7/1979 | Yonezawa | 525/100 |
| 4,579,966 | 4/1986 | De Pasquale et al. | 556/482 |

*Primary Examiner*—Paul F. Shaver

[57] ABSTRACT

Disclosed is a process for manufacturing organosilanes by contacting an olefin with a silane in the presence of an azo compound.

14 Claims, No Drawings

METHOD FOR MANUFACTURING ORGANOSILANES

BACKGROUND OF THE INVENTION

This invention relates to the manufacture of organosilanes by contacting an olefin with a silane in the presence of an azo compound, i.e., free radical initiator.

There are generally three methods for adding an olefinic compound to a silane. They are a Grignard method, a precious metal catalyst route and a free-radical initiator route using peroxides or azo compounds. Each of the prior art processes suffers from various deficiencies. For example, they are expensive and the reaction may proceed very slow. Also, selectivities and yields are significantly lower. Undesirable byproducts may be produced. Finally, an additional recovery and/or recycle of unused silane may be required. U.S. Pat. No. 2,570,462 discloses preparation of organohalosilanes under substantially atmospheric or a slight additional pressure of an inert gas. Therein, reaction times are long, yields are low and excessively disproportional quantities of reactants are used. Further improvements are desirable particularly for a more efficient and economical process.

The present invention meets these needs.

SUMMARY OF THE INVENTION

In accordance with this invention there is provided a process for preparing an organosilane comprising contacting (i) at least one olefin having an olefinic double bond aliphatic in character between two carbons and having hydrogen on at least one of the doubly bonded carbons with (ii) at least one silane of the formula:

$H_aSiR_bX_c$ wherein

H is hydrogen;

R is independently selected from alkyl, alkoxy, aryl, aryloxy, oxysilyl, cycloalkyl, perhaloalkyl and the like;

X is a halogen selected from fluoride, chloride, bromide or iodide;

a is independently 1 to 3;

b and c are independently 0 to 3; and a+b+c=4 in the presence of (iii) at least one azo compound of the formula

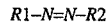

R1–N=N–R2 wherein R1 and R2 are the same or different and are selected from the group consisting of cyanoalkyl, cyanocycloalkyl, alkoxycyanoalkyl, heterocyclo alkyl, alkyl alkoxy ester, aryl alkoxy esters, alkyl aroyl esters, aryl aroyl esters, substituted and unsubstituted alkyl amides, cyanocarboxylic acids, carbamoyl and the like, wherein (iii) is in the amount of about 5% or less, based on a stoichiometric amount of reactants, under pressure in the range of about 30 to about psig at a temperature in the range of about 50° C. to 120° C. for about 10 hours or less;

wherein (ii) is supplied in excess of about 0 to about 100% in amount stoichiometrically required for reacting (i). The reactants are mixed together in a reaction vessel prior to heating. Alternatively, the olefin and azo compounds are added slowly to the silane during the reaction.

The method employed in the process of this invention involves the use of azo compounds and is characterized by the following advantages which, cumulatively render this process preferable to methods previously employed:

1. reactions proceed safely, quickly and with substantially quantitative yields;
2. the initiators are highly selective for the desired products and requires less of the initiator;
3. no separation of initiator is necessary since formation of byproducts is minimal and the products from the initiators do not harm the system, and, more particularly, do not interfere in a subsequent reaction to produce an alkylalkoxysilane and recovery of the same;
4. no undesirable color is introduced into the final products by initiator or byproduct; and
5. inexpensive, more efficient and may optionally eliminate an additional recovery and/or recycle step.

It has been further found that the use of increased autogenous pressure, in combination with select azo compounds, or a mode of addition of the reactants, dramatically increases reaction rate while maintaining high yields and high selectivities.

DETAILED DESCRIPTION

The olefins suitable for use in the present invention include organic compounds having an olefinic double bond aliphatic in character between two carbons and having hydrogen on at least one of the doubly bonded carbons. Aliphatic and cycloaliphatic hydrocarbons, $C_2$–$C_{20}$, can be used. In particular, the olefin is in the form of

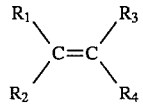

wherein R1–R4 are independently selected from the group consisting of hydrogen, halogen (fluorine), alkyl, alkenyl, cycloalkyl, aryl, alkoxy, aryol, hydrocarbyl, perhaloalkyl and the like. Preferred are 1-hexene, 1-octene, 1-octadecene and cyclohexene. R moieties can be substituted, as will be appreciated by one skilled in the art, provided the substituents do not interfere with the reactants, reaction mechanism, or the reaction products. Also preferred are $C_2$–$C_{20}$ aliphatic olefins containing fluorine. Mixtures of $C_2$–$C_{20}$ olefins may also be used.

The silanes can be defined by the formula:

$H_aSiR_bX_c$ wherein

H is hydrogen; and

R is independently selected from alkyl, alkoxy, aryl, aryloxy, oxysilyl and the like. For example, methyl, methoxy, ethyl, ethoxy, phenyl, phenoxy and the like can be used. R moieties can be substituted, as will be appreciated by one skilled in the art, provided the substituents do not interfere with the reactants, reaction mechanism, or the reaction products. For example, R can be substituted with alkyl, cydoalkyl, aryl, alkoxy, aryloxy, halo, perhaloalkyl and the like.

X is a halogen selected from fluoride, chloride, bromide or iodide;

a is independently 1 to 3;

b and c are independently 0 to 3; and a+b+c=4.

For example, silanes useful for carrying out the invention include halogenated silanes such as chlorinated silanes, particularly trichlorosilane, dichlorosilane, dichloromethylsilane, dichloroethylsilane, dichloromethoxysilane, chlorodimethoxysilane and the like. Mixtures of silanes are contemplated equivalents. If the starting silanes are alkoxysilanes such as triethoxysilane, trimethoxysilane and the like, which possess a hydrogen radical bound to the silicon, then the reaction of the starting silane with the olefin provides directly an alkylalkoxysilane.

Useful azo compounds have the following formula:

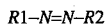

wherein R1 and R2 are the same or different and are selected from the group cyanoalkyl, cyanocycloalkyl, alkoxycyanoalkyl, heterocyclo alkyl, alkyl alkoxy esters, aryl alkoxy esters, alkyl aroyl esters, aryl aroyl esters, substituted and unsubstituted alkyl amides, cyanocarboxylic acids, carbamoyl and the like. Mixtures of azo compounds are contemplated equivalents. An elementary stage of free radical formation is shown below for the class of azo compounds contemplated in the process of this invention:

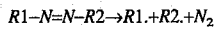

The azo initiators are commercially available, for example, from E. I. du Pont de Nemours and Company and Wako Pure Chemical Industries, Ltd. Representative examples of azo initiators include, but are not limited thereto:

2,2'-azobis(2,4-dimethylpentanenitrile)

2,2'-azobis(2-methylpropanenitrile)

2,2'-azobis(2-methylbutanenitrile)

1,1'-azobis(cyclohexanecarbonitrile)

2,2'-azobis(N,N'-dimethyleneisobutylramidine)dihydrochloride 2,2'-azobis(2-amidinopropane )dihydrochloride 2,2'-azobis(N,N'-dimethyleneisobutylramidine)

4,4'-azobis(4-cyanopentanoic acid)

2,2'-azobis(2-methyl-N-(1,1-bis(hydroxymethyl)-2-hydroxyethyl)propionamide)

2,2'-azobis(2-methyl-N-(1,1-bis(hydroxymethyl)ethyl)propionamide)

2,2'-azobis(2-methyl-N-(2-hydroxyethyl )propionamide)

2,2'-azobis(isobutylramide)dihydrate 2,2'-azobis(4-methoxy-2,4-dimethylvaleronitrile)

dimethyl-2,2'-azobisisobutyrate 2-(carbamoylazo)isobutylronitrile 2,2'-azobis(2,4,4-dimethylpentane)

2-phenylazo-2,4-dimethyl-4-methoxyvaleronitrile and 2,2'-azobis(2-methylpropane).

Particularly useful azo initiators include 2,2'-azobis(2-methylpropanenitrile), 2,2'-azobis(2-methylbutanenitrile) and 1,1'-azobis(cyclohexanecarbonitrile), sold under the trade names Vazo® 64, Vazo® 67 and Vazo® 88, respectively, available from E. I. du Pont de Nemours and Company. These compounds form highly active radicals that will abstract a hydrogen radical from the silane reactant directing the reaction along a desired pathway.

In this aspect of the present invention, all of the reactants can be mixed in a pressure reaction vessel prior to heating. Typically an excess of silane, about 0 to 100%, is added, relative to the stoichiometric amount of olefin, preferably, about 50 to 100% excess, and more preferably about 75 to 100% excess is added if higher yields within shorter reaction times are desirable. It will be appreciated by those skilled in the art that an excess of silane, about 0–100%, preferably about 10 to 50% excess and more preferably about 10 to 20% excess is added if cost reduction due to silane recovery and recycle is a factor. The amount of azo compound added is typically about 5% or less, based on the stoichiometric amount of reactants (olefin and silane % by weight), preferably about 0.5 to 3% and more preferably about 1 to 2%.

The contents of the reaction vessel are stirred and heated typically at about 50° C. to 120° C., preferably 80° C. to 120° C., for about 10 hours or less, preferably for about 8 hours or less and more preferably for about 3 to 5 hours. The reaction temperature is dependent on the azo compound being used. It has been discovered that a specific range of temperature for the azo compounds is critical for running the reaction. That is, if the reaction temperature is too low the reaction does not take place. Concomitantly, if the temperature is too high, decomposition of the azo compound occurs too rapidly and initiation of the reaction is ineffective. For example, the temperature range for Vazo® 64 and Vazo® 67 is about 85° C. to 100° C. and preferably about 90° C. to 95° C. The temperature range for Vazo® 88 is about 95° C. to 110° C. and preferably about 100° C to 105° C. Typically, a pressure of 30–400 psig is generated, preferably 50 to 200 psig, and more preferably 60 to 100 psig. "Autogenous" is defined herein to refer to self generated pressure and pressure produced without external influence or aid such as addition of an inert gas. The pressure generated is autogenous and is established in this embodiment by heating, i.e., the reaction temperature, and the $N_2$ liberated from the azo compound as the reaction progresses. After completion of the reaction, the reaction vessel is cooled to ambient temperature and any excess starting silane is removed from the reaction vessel by any suitable means, for example, by purging the vessel with an inert gas such as nitrogen, helium, argon and the like, and/or by placing the vessel under vacuum. The silane, if in excess, can then be recovered and purified, for example, by distillation for later use.

A product from the reaction of the olefin and a halogenated silane is an alkylhalosilane and is useful as an intermediate to prepare the corresponding alkylalkoxysilane. An alkylhalosilane can be reacted with an alcohol such as ethanol, methanol, n-propyl alcohol, iso-propyl alcohol, n-butyl alcohol, iso-butyl alcohol, tert-butyl alcohol, 2-ethylhexanol, phenol, substituted phenol and the like to provide a corresponding alkylalkoxysilane in which the alkyl compound is substituted with trimethoxysilane, triethoxysilane, and the like in accordance with the alcohol used as described above using conventional methods. Other than removing the unreacted silane, no purification of the alkylhalosilane is necessary before reacting an alkylhalosilane prepared as described above with an alcohol since the impurities present, which can include unreacted starting materials and azo decomposition products, do not interfere in producing the alkylalkoxysilane. Such a process can involve heating from a stoichiometric to an excess amount of alcohol to refluxing temperature. An alkylhalosilane can be fed from a location above the reaction vessel to a packed column which acts as a reaction zone. The alkylhalosilane and alcohol vapor react in the packed column to produce the corresponding alkylalkoxysilane and hydrogen halide. One or more condensers can be present to prevent escape of the reactants from the system. The alkylalkoxysilane product will condense and return to the reaction vessel where no further chemical reaction occurs. The hydrogen halide can be swept from the reaction system by an inert gas purge, such as nitrogen and/or by using vacuum. After all of the silane reactant has been added, refluxing of the contents of the reaction vessel may continue for about 0–5 hours. The product alkylalkoxysilane can be purified by any known method such as distillation.

The alkylhalosilanes and alkylalkoxysilanes of this invention can be used in applications relating to coatings for textiles, plastics, building materials, industrial equipment, household electric appliances, leather and wood products. These silanes can also be used in the preparation of semiconductors, adhesives, sealants, lubricants and hydraulic fluids.

An alternative embodiment of this invention for obtaining faster reaction times involves a mode of addition of the reactants. It has been discovered that when an olefin and azo compound are added intermittently or continuously to either stoichiometric amounts or slight excess of silane in the amount of about 50% excess or less, preferably about 20% excess or less and more preferably about 10% excess or less, reaction times have been diminished. The olefin and azo compound can be added to the silane as a mixture or separately. In carrying out this alternative embodiment, the silane is sealed in a reaction vessel. A stoichiometric amount of olefin and an amount of azo compound as described above are mixed together and this mixture is charged to a feed tank or the olefin and the azo compound can be added separately. The silane in the reaction vessel is stirred and heated as above. The pressure generated is described above but is further established by pumping the olefin and azo compound to the reactor. The olefin/azo is added to the reaction vessel slowly, i.e., so that there is no excess accumulation of olefin. After addition of the olefin/azo mixture is complete, the reaction vessel can be stirred for an additional 1–5 hours at the temperature described above. The reaction vessel is then cooled to ambient temperature and the process continues as described above. However, in this embodiment, the need for recovery and recycle of excess silane has been minimized or eliminated.

Frequently, the azo compound will not completely dissolve in the olefin. Therefore a slurry of the olefin and azo compound may be fed to the reaction vessel. The azo compound remains suspended in the olefin by agitation.

In yet another aspect of the invention, it has been discovered that high yields can be achieved in short reaction times by adding a stoichiometric amount or slight excess of silane of 50% or less preferably 10% or less, and the azo compound to the olefin at reflux at atmospheric or elevated pressures. Alternatively, adding a resulting product of the reaction, such as octyltrichlorosilane, of the olefin and silane at the beginning of the reaction in an amount from about 25 to 75%, based on reactor contents at the beginning of the reaction, also achieves high yields in short reaction times because this essentially uses the product as a solvent to reach a higher temperature as described above.

To give a clearer understanding of the invention, the following Examples are construed as illustrative and not limitative of the underlying principles of the invention in any way whatsoever.

EXAMPLES

Example 1

A 600 ml cylindrical pressure reactor made of Hastelloy® and equipped with a double-paddle agitator, a thermocouple, a pressure gauge, heating mantle, injection port (dip tube) and a discharge port on a head space opening to the atmosphere through an isopropanol trap followed by a dry-ice trap was used.

To this reactor was added 1-octene (1 mole, 112 g, 160 ml), trichlorosilane (2 mole, 270 g, 200 ml, 100% excess), and 1,1'-azobis(cyclohexanecarbonitrile) polymerization initiator (Vazo® 88, 2.5 g, 1% of stoichiometric reactants), and the reactor was sealed. The mixture in the reactor was heated with stirring to 100° C. and kept at 100° C.–105° C. for 4 hours. The reactor pressure was at 65–70 psig during the run. This pressure was vented to the atmosphere through traps to remove the remaining trichlorosilane (TCS). This was followed by nitrogen purge and vacuum. A Gas Chromatography (GC) analysis showed that the product mixture contained >99.5% octyltrichlorosilane (OTCS) and isomers, and <0.03% 1-octene.

Example 2

To the reactor described in Example 1 was added the same ingredients, except 5 g Vazo® 88 (2% of stoichiometric reactants) instead of 2.5 g used in Example 1. The mixture was again heated with stirring to 100° C., but kept at 100° C.–105° C. for only 3 hours. The pressure was 60–80 psig during the run. The remaining TCS was again removed by venting, nitrogen purge and vacuum. A GC analysis showed that the mixture again contained >99.5% OTCS and isomers, with <0.01% 1-octene.

Example 3

To the reactor described in Example I was added 1-octene (1.05 mole, 118 g, 165 ml), TCS (2.05 mole, 276 g, 206 ml, , ~100% excess), and 2,2'-azobis( 2-methylbutanenitrile) polymerization initiator (Vazo® 67, 5.3 g, 2% stoichiometric reactants), and the reactor was sealed. The mixture in the reactor was heated to 80° C. and kept at 80° C.–85° C. for 3 hours. The pressure was 60–100 psig during the run. The remaining TCS was again removed by venting, nitrogen purge and vacuum. A GC analysis showed that the mixture contained >97% OTCS and isomers and <0.7% 1-octene.

Example 4

To the reactor described in Example 1 was added 1-octene (1 mole, 112 g, 160 ml), TCS (2 mole, 270 g, 200 ml, 95 % excess), and 2,2'-azobis(2-methylpropanenitrile polymerization initiator (Vazo® 67, 5.3 g, 2% stoichiometric reactants), and the reactor was sealed. The mixture in the reactor was heated to 80° C. and kept at 80° C.–85° C. for 3 hours. The pressure was 60–65 psig during the run. The remaining TCS was again removed by venting, nitrogen purge and vacuum. A GC analysis showed that the mixture contained >97% OTCS and isomers and <0.7% 1-octene.

Example 5

A 1-liter glass resin kettle with a lid containing four standard taper ground glass joints was equipped with a magnetic stirring bar, heating mantle, solids addition funnel, thermocouple, sampling system, and condenser. The condenser was connected to a 500 ml liquid addition funnel which was topped with a Dewar condenser. The outlet of the Dewar condenser was connected to a dry-ice trap. The entire assembly was purged with nitrogen prior to the reaction and the reaction run at atmospheric pressure using only a slight positive pressure of nitrogen to maintain an inert atmosphere.

The 1-liter resin kettle was charged with 1-octene (2 mole, 229 g, 320 ml). The solids addition funnel was charged with Vazo® 64 (11 g, 2% of stoichiometric reactants). The liquid addition funnel was charged with trichlorosilane (2.2 mole, 301 g, 224 ml, 10% excess). The condenser on the resin kettle was cooled to −10° C. 1-octene in kettle was stirred while being heated. Once the kettle temperature exceeded 95° C., enough TCS was added to 1-octene to bring the kettle temperature to 90° C.–95° C. Small quantities of Vazo® 64 were added at certain intervals to keep the reaction running. The temperature was maintained between 90° C.–95° C. by adding TCS.

The reaction was continued until all the Vazo® and TCS was added. At this point, the temperature was allowed to rise to 125° C., then held for 1 hour. The total reaction time was 10 hours. The reaction mixture was then cooled to ambient temperature and the product sampled. A GC analysis showed that the reaction mixture contained >98% OTCS and isomers, and ~1.6% 1-octene. This exemplifies an improvement in operating at atmospheric pressure which involves feeding trichlorosilane and the azo compound to 1-octene at reflux. The advantage of this mode is that very high yields can be achieved while using a slight excess of silane.

Example 6

To the product left in the resin kettle from Example 5, was added 1-octene (2 mole, 229 g, 320 ml). The equipment and procedure described in Example 5 was used. To the mixture in the resin kettle were added TCS (2.2 mole, 301 g, 224 ml 10% excess) and Vazo® 64 (7 g, ~1% of reactants). The reaction was maintained at atmospheric pressure under a pad of slight positive nitrogen pressure in accordance with standard inert atmosphere lab techniques. The total reaction time was 5 hours. A GC analysis showed that the reaction mixture contained >96% OTCS and isomers, and ~2.3% 1-octene. This exemplifies an alternative improvement in operating at atmospheric pressure which involves adding some of the reaction product, octyltrichlorosilane, at the beginning of the reaction. This essentially uses the product as the solvent. The advantage of this method is that higher reaction temperatures can be reached. At higher temperatures, the reaction proceeds more rapidly because the azo compound is more effective and more silane is available in solution.

Example 7

The equipment described in Example 5 was set up to ethoxylate the product obtained in Example 6. A packed distillation column section was placed between the kettle and the condenser. The resin kettle was charged with anhydrous ethanol (11.6 mole, 539 g, 690 ml, 10% excess). The liquid addition funnel was charged with OTCS (3.5 mole, 865 g, 810 ml). The condenser on the kettle was cooled to −10° C. Stirring was started and the kettle contents were brought to reflux. OTCS was added drop-wise over 5 hours and was ethoxylated in the packed column by contacting vaporized ethanol. The product formed in the packed column would fall in the resin kettle. After 3 hours of additional refluxing, the mixture in the pot was sampled. A GC analysis showed that the reaction mixture contained 92.5% octyltriethoxysilane (OTES) and isomers, 2.5% ethanol and 2% 1-octene. The conversion of OTCS to OTES was essentially quantitative which brought the conversion of 1-octene to OTES to ~95%.

Example 8

To the 600 ml pressure reactor described in Example 1 was added 1-octadecene (190 g, 0.75 mole), trichlorosilane (152 g, 1.12 mole, ~50% excess), and Vazo® 88, (5 g, 1.5% of stoichiometric reactants). The mixture was heated with stirring to 100° C. and kept at 100° C.–105° C. for 3 hours. The pressure was between 90–140 psig during this run. The excess TCS was removed as described in Example 1. The GC analysis showed that the reaction mixture contained about 90% octadecyltrichlorosilane and isomers thereof, and about 3% 1-octadecene.

Example 9

The reaction described in Example 8 was repeated using the same reactor and the procedure, except using 1-octadecene (169 g, 0.67 mole), trichlorosilane (200 g, 1.47 mole, ~120% excess), and Vazo® 88 (7 g, 2.7% of stoichiometric reactants). The mixture was heated with stirring to 100° C. and kept at 100° C.–102° C. for 5 hours. The pressure was 60 and 80 psig during the run. The excess TCS was removed as described in Example 1. A GC analysis showed that the reaction mixture contained about ~98% octadecyltrichlorosilane and isomers thereof, and about ~1% 1-octadecene.

Comparative Example 10

A single neck, 50 mL roundbottom flask was equipped with a magnetic stirring bar, heating mantle and condenser. The condenser was topped with a Claisen adapter and a polytetrafluoroethylene clad thermocouple was inserted through the Claisen adapter and condenser to reach the liquid layer of the flask. The other arm of the Claisen adapter was topped with a Dewar condenser. The entire assembly was purged with nitrogen prior to the reaction and the reaction run atmospheric pressure using only a slight positive pressure of nitrogen to maintain an inert atmosphere. The round bottom flask was charged with 1-octene (11.5 g, 0.1 mole) and trichlorosilane (TCS) (13.5 g, 0.1 mole) and Vazo® 64 (0.25 g, 1% of reactants). Stirring was initiated and flask content were heated to the reflux temperature. The reaction mixture initially began to reflux at 45° C. and the reflux temperature rose to 120° C. over the 10 hour period the reaction was allowed to proceed. A GC analysis showed that the product contained about 75% OTCS and isomers thereof, and about 10% 1-octene.

The above process was repeated using 2,2'-azobis(2,4-dimethylpentanenitrile), Vazo® 52, another polymerization initiator available from E. I. du Pont de Nemours and Company. In this experiment, 1-octene (22.5 g, 0.20 mole), TCS (27.1 g, 0.20 mole) and Vazo® 52 (0.5 g, 1% of reactants) were placed in a 100 mL single-necked round bottom flask. Stirring was initiated and the flask contents were heated to the reflux temperature. The reaction mixture initially began to reflux at 45° C. and the reflux temperature rose to 120° C. over the 15 hour period the reaction was allowed to proceed. A GC analysis showed that the product contained 65% OTCS and isomers thereof, and about 25% 1-octene.

Example 11

The process of Comparative Example 10 was repeated using 100 mL single-neck, round bottom flask and 1-octene (11.5 g, 0.1 mole), TCS (15 g, 0.11 mole, 10% excess), OTCS (25 g, 0.1 mole), and Vazo® 52 (1.5 g, 3% of the initial reaction mix). After refluxing at atmospheric pressure for 3 hours, a GC analysis showed that the reaction mixture contained about 84% OTCS and isomers thereof and about 15% 1-octene. To this reaction mixture was added Vazo® 64 (0.5 g, 1% of initial reaction mix) and the reaction mixture was refluxed for an additional 2 hours. A GC analysis at this point showed that the mixture now contained about 95% OTCS and isomers thereof, and about 3% 1-octene.

The above process was repeated using another 100 mL roundbottom flask and same amounts of materials (1-octene, TCS, and OTCS), except combining Vazo® 52 (0.75 g, 1.5% initial reaction mix) and Vazo® 64 (0.5 g, 1% of initial reaction mix) as initiators. After refluxing the reaction mixture for 5 hours, a GC analysis showed that it contained about 94% OTCS and isomers thereof, and about 4% 1-octene.

This exemplifies an alternative improvement in operating at atmospheric pressure. It involves using some of the reaction product, OTCS, as the solvent for the reaction to raise the boiling point of the initial reaction mixture. The reaction progresses rapidly from the very beginning due to the elevated reflux temperature.

Example 12

A 2-neck, 250 mL roundbottom flask was equipped with a magnetic stirring bar, heating mantle, solids addition funnel, and condenser. The top of the condenser was fitted with a Claisen adapter and a polytetrafluoroethylene clad thermocouple was inserted through he straight neck of the Claisen adapter and condenser to reach the liquid layer in the flask. The other neck of the Claisen adapter was fitted with a liquid addition funnel above which was fitted a Dewar condenser. The entire assembly was purged with nitrogen prior to the reaction and the reaction run at atmospheric pressure using only a slight positive pressure of nitrogen to maintain an inert atmosphere. The solids addition funnel was charged with Vazo® 64 (3 g, ~2% of stoichiometric reactants). The liquid addition funnel was charged with trichlorosilane (75.3 g, 56 mL, 0.55 mole, ~10% excess). The reaction flask was charged with 1-octene (57.3 g, 0.5 mole).

The reaction was started by adding ~6 ml of TCS and ~0.5 g Vazo® 64 to the 1-octene with stirring and heating the resulting mixture. The reaction mixture refluxed at about 105° C. After about 1 hour, TCS was added dropwise over the next 4.5 hours. During this time, Vazo® 64 was added intermittently to the reaction mixture. The temperature of reflux was maintained between ~85° C. to 95° C. during the TCS addition. After all the TCS was added, the reaction was heated for another 4 hours at the end of which time the reflux temperature had reached about 130° C. A GC analysis showed that the produced contained >96% OTCS and isomers thereof, and about 1.6% 1-octene.

This exemplifies an improvement in operating at atmospheric pressure which involves feeding trichlorosilane and the azo compound to 1-octene at reflux. The temperature of the mixture at reflux is maintained so as to be at the optimum temperature range for the specific azo compound used to initiate the reaction. The advantage of this mode is that high yields can be achieved while using only a slight excess of silane.

Having thus described and exemplified the invention with a certain degree of particularity, it should be appreciated that the following claims are not to be limited but are to be afforded a scope commensurate with the wording of each element of the claims and equivalents thereof.

We claim:

1. A process for preparing an organosilane comprising contacting (i) at least one olefin having an olefinic double bond aliphatic in character between two carbons and having hydrogen on at least one of the doubly bonded carbons, with (ii) at least one silane of the formula:

$$H_aSiR_bX_c$$

wherein H is hydrogen;
R is independently selected from the group consisting of alkyl, alkoxy, aryl, aryloxy, oxysilyl, cycloalkyl and perhaloalkyl;
X is a halogen selected from the group consisting of fluoride, chloride, bromide and iodide;
a is independently 1 to 3;
b and c are independently 0 to 3; and
a+b+c=4;
in the presence of (iii) at least one azo compound of the formula:

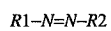

$$R1-N=N-R2$$

wherein R1 and R2 are the same or different and are selected from the group consisting of cyanoalkyl, cyanocycloalkyl, alkoxycyanoalkyl, heterocyclo alkyl, alkyl alkoxy esters, aryl alkoxy esters, alkyl aroyl esters, aryl aroyl ester, substituted and unsubstituted alkyl amides, cyanocarboxylic acids and carbamoyl;
wherein (iii) is in the amount of about 5% or less, based on a stoichiometric amount of reactants, under pressure in the range of about 30 to about 400 psig at a temperature in the range of about 50° to 120° C. for about 10 hours or less; and wherein (ii) is supplied in excess of about 0 to about 100% in amount stoichiometrically required for reacting (i) to produce (iv) the organosilane.

2. The process of claim 1 wherein (i) has 2–20 carbons, (ii) is a halogenated silane and (iii) is selected from the group consisting of
2,2'-azobis(2,4-dimethylpentanenitrile),
2,2'-azobis(2-methylpropanenitrile),
2,2'-azobis(2-methylbutanenitrile),
1,1'-azobis(cyclohexanecarbonitrile),
2,2'-azobis(N,N'-dimethyleneisobutylramidine)dihydrochloride,
2,2'-azobis(2-amidinopropane)dihydrochloride,
2,2'-azobis(N,N'-dimethyleneisobutylramidine),
4,4'-azobis(4-cyanopentanoic acid),
2,2'-azobis(2-methyl-N-(1,1-bis(hydroxymethyl)-2-hydroxyethyl)propionamide),
2,2'-azobis(2-methyl-N-(1, 1-bis(hydroxymethyl)ethyl)propionamide),
2,2'-azobis(2-methyl-N-(2-hydroxyethyl)propionamide),
2,2'-azobis( isobutyramide )dihydrate,
2,2'-azobis(4-methoxy-2,4-dimethylvaleronitrile),
dimethyl-2,2'-azobisisobutyrate,
2-(carbamoylazo)isobutyronitrile,
2,2'-azobis(2,4,4-dimethylpentane),
2-phenylazo-2,4-dimethyl-4-methoxyvaleronitrile, and
2,2'-azobis(2-methylpropane).
wherein the pressure is in the range of about 50 to about 200 psig at a temperature in the range of about 80° to 110° C. for about 8 hours or less.

3. The process of claim 2 wherein (i) is 1-octene, (ii) is trichlorosilane and (iii) is 2,2'-azobis(2-methylpropanenitrile) and the pressure is about 60 to 100 psig at a temperature in the range of about 90° to 95° C. for about 3 to 5 hours.

4. The process of claim 2 wherein (i) is 1-octene, (ii) is trichlorosilane and (iii) is 1,1'-azobis(cyclohexanecarbonitrile) and the pressure is about 60 to 100 psig at a temperature in the range of about 100° to 105° C. for about 3 to 5 hours.

5. The process of claim 2 wherein (i) is 1-octene, (ii) is trichlorosilane and (iii) 2,2'-azobis(2-methylbutanenitrile) and the pressure is about 60 to 100 psig at a temperature in the range of about 90° to 95° C. for about 3 to 5 hours.

6. The process of claim 2 wherein (i) is 1-octadecene, (ii) is trichlorosilane and (iii) is 2,2'-azobis(2-methylpropanenitrile) and the pressure is about 60 to 100 psig at a temperature in the range of about 90° to 950° C. for about 3 to 5 hours.

7. The process of claim 2 wherein (i) is 1-octadecene, (ii) is trichlorosilane and (iii) is 1,1'-azobis(cyclohexanecarbonitrile) and the pressure is about 60 to 100 psig at a temperature in the range of about 100° to 105° C. for about 3 to 5 hours.

8. The process of claim 2 wherein (i) is 1-octadecene, (ii) is trichlorosilane and (iii) 2,2'-azobis(2-methylbutanenitrile) and the pressure is about 60 to 100 psig at a temperature in the range of about 90° to 95° C. for about 3 to 5 hours.

9. The process of any of claims 1–8 wherein the reactants are mixed together in a reaction vessel prior to heating.

10. The process of any of claims 1–8 wherein the olefin and azo compounds are added slowly to the silane during the reaction.

11. The process of any of claims 1–8, wherein the organosilane is (iv) an alkylhalosilane and, further comprising the step of reacting (iv) with (v) an alcohol to (vi) a corresponding alkylalkoxysilane.

12. The process of claim 11 wherein (iv) is octyltrichlorosilane, (v) is ethanol and (vi) is octyltriethoxysilane.

13. A process for preparing an organolsilane comprising adding, in sequence, a silane of the formula

$$H_aSiR_bX_c$$

wherein H is hydrogen;

R is independently selected from the group consisting of alkyl, alkoxy, aryl, aryloxy, oxysilyl, cycloalkyl and perhaloalkyl;

X is a halogen selected from the group consisting of fluoride, chloride, bromide and iodide;

a is independently 1 to 3;

b and c are independently 0 to 3; and a+b+c=4;

in excess of 50% or less, and an azo compound selected from the group consisting of 2,2'-azobis(2-methylpropanenitrile) 2,2'-azobis(2-methylbutanenitrile) and 1,1'-azobis(cyclohexanecarbonitrile) to an olefin under pressure of 200 psig and less.

14. A process for preparing an organosilane comprising contacting (i) an olefin with (ii) a silane of the formula

$$H_aSiR_bX_c$$

wherein H is hydrogen;

R is independently selected from the group consisting of alkyl, alkoxy, aryl, aryloxy, oxysilyl, cycloalkyl and perhaloalkyl;

X is a halogen selected from the group consisting of fluoride, chloride, bromide and iodide;

a is independently 1 to 3;

b and c are independently 0 to 3; and a+b+c=4;

supplied in excess of 50% or less in an amount stoichoimetrically required for reacting (i), in the presence of (iii) at least one azo compound selected from the group consisting of 2,2'-azobis(2-methylpropanenitrile), 2,2'-azobis(2-methylbutanenitrile) and 1,1'-azobis(cyclohexanecarbonitrile), and (iv) an organosilane, under pressure of 200 psig and less.

* * * * *